US012765930B2

(12) United States Patent
Kluge et al.

(10) Patent No.: US 12,765,930 B2
(45) Date of Patent: Oct. 20, 2026

(54) KIT FOR PRODUCING AND EXTRUDING BONE CEMENT, AND METHOD

(71) Applicant: Heraeus Medical GmbH, Wehrheim (DE)

(72) Inventors: Thomas Kluge, Wehrheim (DE); Sebastian Vogt, Wehrheim (DE); Ekaterini Hohmann, Wehrheim (DE)

(73) Assignee: Heraeus Medical GmbH, Wehrheim (DE)

(*) Notice: Subject to any disclaimer, the term of this patent is extended or adjusted under 35 U.S.C. 154(b) by 30 days.

(21) Appl. No.: 18/965,528

(22) Filed: Dec. 2, 2024

(65) Prior Publication Data

US 2025/0186095 A1 Jun. 12, 2025

(30) Foreign Application Priority Data

Dec. 7, 2023 (EP) .................................... 23214789

(51) Int. Cl.
*A61B 17/88* (2006.01)

(52) U.S. Cl.
CPC ................................ *A61B 17/8802* (2013.01)

(58) Field of Classification Search
CPC ............ A61B 17/8802; A61B 17/8805; A61B 17/8808; A61B 17/8811; A61B 17/8816; A61B 17/8825; A61B 17/8833; A61B 17/8836

See application file for complete search history.

(56) References Cited

U.S. PATENT DOCUMENTS

| | | | |
|---|---|---|---|
| 589,344 | A | 8/1897 | Eccleston |
| 4,671,263 | A | 6/1987 | Draenert |
| 4,973,168 | A | 11/1990 | Chan |
| 5,100,241 | A | 3/1992 | Chan |
| 5,344,232 | A | 9/1994 | Nelson et al. |
| 5,586,821 | A | 12/1996 | Bonitati et al. |
| 5,624,184 | A | 4/1997 | Chan |

(Continued)

FOREIGN PATENT DOCUMENTS

| | | |
|---|---|---|
| CN | 213190021 U | 5/2021 |
| CN | 218220290 U | 1/2023 |

(Continued)

OTHER PUBLICATIONS

Charnley et al., Anchorage of the femoral head prosthesis of the shaft of the femur, The Journal of Bone and Joint Surgery, vol. 42-B, No. 1, pp. 28-30 (1960), Feb. 1, 1960.

*Primary Examiner* — Si Ming Ku
(74) *Attorney, Agent, or Firm* — Dicke, Billig & Czaja, PLLC

(57) ABSTRACT

A kit for producing and extruding bone cement, to a use of a kit, and to a method. A kit for producing and extruding bone cement comprises a first container which contains a first component for producing bone cement, a second container which contains a second component for producing bone cement, a mixing apparatus for manually mixing the first component and the second component in the first container for the purpose of producing bone cement, and an extruding apparatus for manually extruding the produced bone cement from the first container. In this way, all materials and apparatuses required for the production and extrusion of bone cement are provided together.

15 Claims, 12 Drawing Sheets

(56) References Cited

U.S. PATENT DOCUMENTS

| | | | |
|---|---|---|---|
| 5,638,997 | A | 6/1997 | Hawkins et al. |
| 5,997,544 | A | 12/1999 | Nies et al. |
| 6,033,105 | A | 3/2000 | Barker et al. |
| 6,676,663 | B2 | 1/2004 | Higueras et al. |
| 6,709,149 | B1 | 3/2004 | Tepic |
| 8,662,736 | B2 | 3/2014 | Vogt et al. |
| 8,865,777 | B2 | 10/2014 | Vogt et al. |
| 10,045,806 | B2 | 8/2018 | Vogt et al. |
| 11,109,906 | B2 | 9/2021 | Vogt et al. |
| 11,241,266 | B2 | 2/2022 | Vogt et al. |
| 11,490,940 | B2 | 11/2022 | Vogt et al. |
| 2007/0211565 | A1 | 9/2007 | Plishka et al. |
| 2012/0224452 | A1 | 9/2012 | Melsheimer et al. |
| 2014/0088712 | A1* | 3/2014 | Gage .................. A61B 17/8825 606/279 |
| 2017/0095283 | A1* | 4/2017 | Vogt ........................ B01F 31/40 |
| 2022/0234014 | A1 | 7/2022 | Brockman et al. |
| 2023/0371995 | A1 | 11/2023 | Vogt et al. |

FOREIGN PATENT DOCUMENTS

| | | | |
|---|---|---|---|
| DE | 3640279 | A1 | 6/1987 |
| DE | 19718648 | A1 | 11/1998 |
| DE | 102009031178 | B3 | 9/2010 |
| DE | 102015106899 | B3 | 7/2016 |
| EP | 0692229 | A1 | 1/1996 |
| EP | 0380867 | B1 | 8/1997 |
| EP | 0796653 | A2 | 9/1997 |
| EP | 1005901 | A2 | 6/2000 |
| EP | 1016452 | A2 | 7/2000 |
| EP | 1020167 | A2 | 7/2000 |
| EP | 1886647 | A1 | 2/2008 |
| EP | 1741413 | B1 | 9/2009 |
| EP | 2 404 864 | B1 | 1/2012 |
| EP | 2269718 | B1 | 7/2013 |
| EP | 2393456 | B1 | 1/2015 |
| EP | 2 710 972 | B1 | 4/2016 |
| EP | 2281532 | B1 | 9/2016 |
| EP | 2 711 091 | B1 | 5/2018 |
| EP | 3584005 | A1 | 12/2019 |
| EP | 3054880 | B1 | 1/2020 |
| EP | 3093067 | B1 | 1/2020 |
| EP | 22 174 728 | A1 | 5/2022 |
| EP | 23177508 | A | 6/2023 |
| EP | 4282518 | A1 | 11/2023 |
| WO | 9416951 | A1 | 8/1994 |
| WO | 9426403 | A1 | 11/1994 |
| WO | 9967015 | A1 | 12/1999 |
| WO | 0035506 | A1 | 6/2000 |

* cited by examiner

KIT FOR PRODUCING AND EXTRUDING BONE CEMENT, AND METHOD

CROSS-REFERENCE TO RELATED APPLICATIONS

This application claims priority pursuant to 35 U.S.C. 119(a) to European Patent Application No. 23214789.2, filed Dec. 7, 2023, which application is incorporated herein by reference in its entirety.

FIELD OF THE INVENTION

The invention relates to a kit for producing and extruding bone cement, to a use of a kit, and to a method for using a kit.

BACKGROUND OF THE INVENTION

Bone cement is usually produced by mixing a powder with a liquid. For example, polymethyl methacrylate (PMMA) bone cements are known which are composed of a liquid monomer component and a powder component. The monomer component generally contains the monomer methyl methacrylate and in particular an activator dissolved therein, such as N,N-dimethyl-p-toluidine. The powder component, also referred to as bone cement powder, comprises one or more polymers which are produced on the basis of methyl methacrylate and comonomers such as styrene, methyl acrylate or similar monomers by polymerization, preferably suspension polymerization, and in particular a radiopaque material and/or the initiator dibenzoyl peroxide. When the powder component is mixed with the monomer component, a plastically deformable paste, the actual bone cement (also termed a bone cement paste), is produced, for example by the polymers of the powder component swelling in the methyl methacrylate. When the powder component is mixed with the monomer component, the activator N,N-dimethyl-p-toluidine, for example, reacts with dibenzoyl peroxide to form radicals. The radicals formed can initiate the radical polymerization of the methyl methacrylate. As the polymerization of the methyl methacrylate progresses, the viscosity of the cement can increase until it solidifies.

PMMA bone cements are mainly used for the permanent anchoring of joint endoprostheses in the bone. In general, cement quantities of 50 g to 125 g or more are used to anchor a joint endoprosthesis. The bone cement is needed during the patient's surgery and should be provided promptly. This is the main field of application of the present invention. The field of application of the invention, however, does not lie in the provision of minimal quantities in the range of less than 10 g and/or 10 ml of bone cement for the stabilization of vertebral bodies, as is the case, for example, in kyphoplasty and vertebroplasty. Such minimal quantities can be extruded using simple technical means.

Polymethylmethacrylate bone cements can be mixed in suitable mixing beakers with the aid of spatulas by mixing the cement powder with the monomer liquid. In the process, air bubbles may become incorporated into the bone cement, and can negatively influence the mechanical properties of the hardened bone cement. Other disadvantages are the need to measure the quantities manually, and adequate mixing, which is not always ensured. The features, embodiments and definitions mentioned herein can be combined as desired with the features of the invention.

Vacuum cementing systems are known for preventing air inclusions in the bone cement; of these the following are mentioned by way of example: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, EP 1 886 647 A1, U.S. Pat. No. 5,344,232 A. A further development in cementing technology is represented by cementing systems in which both the cement powder and the monomer liquid are already packaged in separate compartments and are mixed with one another directly before cement application in the cementing system. Such closed fully prepacked mixing systems or similar systems are described, inter alia, in the documents EP 0 380 867 B1, EP 0 796 653 B1, EP 0 692 229 A1, DE 10 2009 031 178 B3, U.S. Pat. Nos. 5,997,544 A, 6,709,149 B1, WO 00/35506 A1 and EP 0 796 653 A2. It is currently necessary to use an external device for pressing out, such as a cartridge press (cement gun). Since such devices are expensive and complicated, they are provided separately, and can then be used in conjunction with the corresponding mixing system. Cleaning and sterilization is then necessary to be able to reuse the device.

Mixing apparatuses in which an external apparatus for pressing out the bone cement is used are disclosed in WO9416951A1, EP1741413B1, EP3054880B1 and DE19718648A1.

Mixing apparatuses in which a vacuum is applied to enable the transportation or mixing of a component or of the bone cement, or similar systems, are known from U.S. Pat. No. 8,662,736B2 and EP3093067B1. EP2393456B1 describes a mixing apparatus in which the liquid is pressed into the powder by means of an overpressure.

Manually operated discharge apparatuses, for example, are based on manually movable lever systems that drive push rods or toothed bars and are connected to the cement cartridges. By repeatedly tilting the levers, the push rod or toothed bar is moved in the direction of the discharge plunger of the cartridge, wherein the discharge plunger, by moving in the direction of the cartridge head, presses the polymethyl methacrylate bone cement out of the cartridge—with the discharge tubes attached in front of it. Such or similar discharge apparatuses are disclosed in U.S. Pat. Nos. 589,344A, 5,638,997A and WO9416951A.

Screw systems are commonly used to remove small amounts of cement up to approximately 10 g of bone cement, and are used to stabilize fractured vertebral bodies. These screw systems known to date have only a low mechanical load-bearing capacity and are not suitable for the discharge of larger quantities of at least 50 g of PMMA bone cement. Examples of such discharging apparatuses or similar apparatuses are the publications U.S. Pat. No. 6,676,663B2, US 2012/224,452A1, CN218220290U and CN213190021U.

SUMMARY OF THE INVENTION

It is the object of the invention to provide a simple and cost-effective solution for producing and extruding bone cement.

The object is achieved by a kit for producing and extruding bone cement according to claim 1, and by a use of a kit and a method according to the independent claims.

To achieve the object, a kit is used for producing and extruding bone cement, comprising:

a first container which contains a first component for producing bone cement, a second container which contains a second component for producing bone cement, a mixing apparatus for manually mixing the first component and the second component in the first container for the purpose of producing bone cement, and, an extruding apparatus for manually extruding the produced bone cement from the first container.

The kit typically contains all the materials and equipment required for the production and the extruding, and can therefore also be referred to as a fully prepackaged mixing system or a "procedure pack". The kit also includes an extruding apparatus. Therefore, the kit is suitable not only for producing bone cement, but also for pressing it out at the site of use. Since conventional extruding apparatuses are expensive and technically complex, they are generally not integrated into a kit.

The kit can be used directly by the medical user, e.g. the operating physician, during the operation. In one embodiment, the kit is designed so that no additional devices or items are necessary to prepare and extrude the bone cement. In another embodiment, the kit is designed such that it can be connected to a vacuum source so that a vacuum can be applied to the first container to mix the bone cement.

In particular, bone cement can be prepared by mixing the first component and the second component. However, it cannot be ruled out that one or more additional substances are present in the production of bone cement. In particular, the first component comprises or is a powder, for example comprising one or more polymers. In particular, the second component comprises or is a liquid, for example a monomer liquid.

The first container encloses a cavity in which the first component is contained and into which the second component can be introduced. The first container may further comprise additional components, such as one or more connecting regions as described below.

In particular, the first container is a closed container. In particular, the first container is designed as a cartridge. The cartridge comprises in particular a cylindrical, for example circular cylindrical, wall. The extruding apparatus can be designed such that a plunger can be pressed into the cartridge from a first side along the longitudinal direction of the cartridge in order to displace the bone cement contained therein. In this way, the bone cement can be extruded on the opposite, second side.

In particular, the second container is a closed container. For example, the second container can be designed as a pouch or ampoule. There may be two or more second containers.

In particular, the extruding apparatus can be operated manually. This means that a manual force can be exerted, in particular from the outside, on the first container, which allows for the bone cement to be extruded in a mechanical way. In particular, the extruding apparatus is designed to be mechanically connected to the first container. Accordingly, for example, the extruding apparatus can only be connected to the first container once the mixing of the bone cement in the first container is completed. The connection between the extruding apparatus and the first container can be reversible, namely manually detachable. Preferably, the extruding apparatus comprises a connecting region, and the first container comprises a connecting region, wherein the two connecting regions can be connected to one another manually and in particular reversibly. In the connected state, bone cement can be extruded from the first container using the extruding apparatus. The connecting regions can be designed, for example, as a thread, as a clamp or, preferably, as a bayonet lock. Both connecting regions then comprise corresponding connecting elements, e.g. in the form of pins. The connecting elements of the first container can be arranged inside a wall of the first container and/or protrude inwards. This makes it possible to extrude bone cement just a few seconds after the completion of mixing. This can save valuable operating time. In addition, the user can start cementing more quickly, so that a longer period of time remains for cementing before the end of the processing phase.

The mixing apparatus is in particular designed to move a mixing element in the first container in order to mix the two components. For example, the mixing apparatus comprises a handle with which the mixing element can be moved in the first container. The handle and mixing element are typically connected via a central and/or axial rod. The movement occurs, for example, up and down along the longitudinal axis of the first container and/or rotating about the longitudinal axis. The mixing element can be a perforated disk which, when moved, displaces parts of the mass in the first container and lets through other parts of the mass in order to achieve mixing. The outer contour of the disk may correspond substantially or completely to the inner contour of the first container so that the disk can be moved like a cylinder in a plunger.

Preferably, the mixing apparatus comprises a connecting region, and the first container comprises a connecting region, wherein the two connecting regions can be connected to one another manually, and in particular reversibly. In the connected state, the components in the first container can be mixed together by the mixing apparatus to produce bone cement.

In one embodiment, the kit further comprises at least one discharge tube for discharging the prepared bone cement, a pressurizer, such as a knee pressurizer and/or a hip pressurizer, a snorkel, such as a knee snorkel and/or a flat snorkel, and/or a vacuum hose for connecting the first container to an external vacuum source. A pressurizer is a connector made of a flexible material such as rubber with which bone cement from the first container can be pressed into body tissues such as cancellous bone. A snorkel is a tubular body for transporting bone cement to a target position, particularly in the region of a joint.

In one embodiment, the mixing apparatus is at least partially arranged in the first container. In other words, at least a part of the mixing apparatus, in particular the mixing element, is located in the first container. This enables particularly space-saving packaging and reduces the number of work steps during use. The mixing apparatus can be pushed as far as possible into the first container. Typically, a handle of the mixing apparatus is located outside the first container. The handle can limit insertion.

The mixing apparatus can be delivered fully assembled, i.e., ready for use. Alternatively, only a part of the mixing apparatus, in particular the adapter unit, is connected to the first container, while a further part of the mixing apparatus, in particular the threaded rod with the handle, is arranged separately. In this case, the threaded rod must be connected to the adapter unit before mixing.

Axial, in the context of the invention, refers to a corresponding longitudinal axis. The axial extension is the length between the opposite ends of the given component. The axial extension of the extruding apparatus therefore refers to the length of the extruding apparatus along its longitudinal axis. Typically, the extruding apparatus is configured to be moved along the longitudinal axis and/or to move bone cement along the longitudinal axis. The axial extension of the first container with the mixing apparatus refers to the length of the group of these two components in the described state in which the mixing apparatus is at least partially arranged in the first container.

In one embodiment, the extruding apparatus has an axial extension A, and the first container with the mixing apparatus has an axial extension B. The following can apply to the ratio A/B: A/B≥0.9, in particular ≥1.0 or ≥1.1 and/or A/B≤1.5, in particular ≤1.4 or ≤1.3.

In other words, the extruding apparatus is at most larger by a factor of 1.5 than the first container with the mixing apparatus. A small extruding apparatus therefore enables a compact kit with small packing dimensions. For example, the extruding apparatus is at most slightly smaller, but typically at least just as large as the first container with the mixing apparatus. This ensures that the bone cement can be at least mostly and in particular completely extruded from the first container, and yet none of the components is excessively long compared to the other components. In particular, the extruding apparatus is however not larger than 1.4 times the first container. This allows a particularly space-saving packing size to be achieved. In addition, a particularly compact shape can be achieved in which the length and width of the kit lie within similar ranges. For example, the length is at most 50%, preferably at most 35% and in particular at most 20% larger than the width. It has been shown that such dimensions are advantageous with regard to transport and installation during use. In addition, stability is increased.

After the bone cement has been completely extruded, the extruding apparatus is typically partially situated in the first container. The axial extension of the first container with the extruding apparatus is C. In one embodiment, the ratio is: C/A≤1.4.

In one embodiment, the maximum height of the kit, in particular of a packaging means of the kit, is less than the length and/or the width. In particular, the height is a maximum of 70% of the length and/or width, preferably a maximum of 55% of the length and/or width. In this way, high stability of the kit is ensured.

In one embodiment, after the bone cement has been completely extruded, the axial extension of the first container with the extruding apparatus located therein, in particular from the outermost point of the first container to the end of the handle of the extruding apparatus on the opposite side, is equal to or less than 1.2 times the axial extension of the extruding apparatus.

The extruding apparatus can have a lever system and/or be designed as a cartridge press. The extruding apparatus can be driven by a gas cartridge, for example as described in EP 2 711 091 B1 and/or EP 2 710 972 B1. Each of these documents is incorporated by reference into this application.

In one embodiment, the extruding apparatus comprises a threaded rod with an external thread, a handle for rotating the threaded rod, and an adapter unit for mechanically connecting to the first container. In particular, the adapter unit comprises a passage opening with an internal thread for the threaded rod. The first container is then correspondingly designed to be mechanically connected to the adapter unit.

In particular, a connecting means of the extruding apparatus is provided on the adapter unit for connection to the first container. In particular, a connection for conjoint rotation is provided at least in the direction of rotation of the threaded rod, such that rotating the threaded rod does not impair or loosen the attachment of the adapter unit to the first container. When the adapter unit is attached to the first container, the axial relative movement of the threaded rod in relation to the adapter unit and thus to the first container causes the end of the threaded rod opposite the handle to penetrate into the first container and thus extrude bone cement out of the first container. In this way, bone cement can be pressed out from the end of the first container opposite the adapter unit.

In one embodiment, a pitch of the external thread is at least 1 mm, preferably at least 3 mm and/or at most 7 mm, preferably at most 5 mm. This has proven to be particularly effective in tests. In one embodiment, an outer diameter of the external thread of the threaded rod is at least 12 mm and/or at most 17 mm. The outer diameter means the maximum diameter measured between the two maximum peaks of the thread turn, i.e., the diameter of an imaginary circular cylinder surrounding the external thread. In particular, the outer diameter is at least 13.5 mm and/or at most 15 mm. In one embodiment, the outer diameter is approximately or exactly 14 mm. An outer diameter of less than 12 mm is not suitable to withstand the forces or moments that occur. An outer diameter that is too large increases friction and thus the force required for discharge. In one embodiment, the internal thread of the adapter unit contains at least 2 threads, preferably at least or exactly 4 threads and/or at most 6 threads, preferably at most 5 threads. In one embodiment, the thread of the threaded rod is a trapezoidal thread. This has proven to be particularly suitable. In one embodiment, the external thread of the threaded rod has a thread depth of at least 1 mm and/or at most 3 mm or 4 mm.

In one embodiment, for exerting pressure on the bone cement in the first container, the extruding apparatus comprises a pressure element on the end of the threaded rod which is opposite the handle. In particular, the pressure element has a flat surface. The pressure element can be designed to exert pressure directly or indirectly. In one embodiment, the pressure element is connected to the threaded rod for conjoint rotation. For example, the pressure element can be screwed onto the threaded rod, welded to it, or connected to the threaded rod by means of a plugged connection. The pressure element can be made entirely or partially of metal or plastic material, for example of glass-fiber-reinforced plastic material and/or polyamide. In one embodiment, the pressure element is constructed in two parts. A first part of the pressure element is connected to the threaded rod for conjoint rotation. A second part of the pressure element is connected to the first part for rotation about the longitudinal axis of the threaded rod. A lubricant such as silicone may be provided between the first part of the pressure element to ensure particularly smooth relative rotation between the first part and the second part. In one embodiment, the second part surrounds the first part at least partially or circumferentially. In other words, the second part forms an undercut behind the first part. This ensures that the first part and the second part do not separate from each other. This prevents axial movement of the second part away from the first part and thus loss of the second part. In particular, a surface of the second part facing the first part and/or a surface of the first part facing the second part is flat and/or smooth. The pressure element and/or each of the parts is in particular resistant to a pressure force of at least 1 kN, preferably 2 kN.

These features enable particularly easy manual discharge of larger quantities of bone cement, such as those required for the fixation of a joint endoprosthesis in human bone tissue. The extruding apparatus can be manufactured completely or partially at low cost by plastic injection molding.

In one embodiment, an outer surface of a thread turn of the external thread is at most 370 $mm^2$. In one embodiment, the outer surface of a thread turn of the external thread is at least 230 $mm^2$.

The outer surface has a strong influence on friction losses when the threaded rod is rotated in the adapter unit, and thus on the force to be applied to discharge the bone cement. The outer surface is a measure of the surface area of the external thread that contacts the internal thread. The resulting friction is accordingly proportional to the outer surface. Tests have shown that it is irrelevant whether a reduction in the outer surface is achieved by reducing the thread depth, increasing the flank angle, reducing the diameter of the threaded rod, reducing the pitch, or other measures or by combinations of different measures. Only the absolute value of the outer surface is relevant.

Due to the reduction in friction according to the invention, even people with less strength can operate the extruding apparatus without difficulty. This is particularly important because the bone cement after mixing continues to solidify over time and therefore the forces required for extruding increase over time. Tests have shown that with the described maximum outer surface of a thread turn of the external thread, it is possible for any user to easily discharge the bone cement by manually rotating the handle. With larger outer surfaces, static friction and sliding friction make discharging very difficult, and therefore result in poor ease of handling. This design allows 125 g of polymethyl methacrylate bone cement, which is typically highly viscous, to be extruded within a few seconds.

The lower limit of the outer surface ensures that the mechanical stability of the threaded rod is maintained. If the outer surfaces are too small, for example, the thread depth or the diameter of the threaded rod will be so small that shearing of the external thread and/or torsion or buckling of the threaded rod can occur.

The pitch of the external thread also influences the force required for discharge. The pitch of the external thread is the distance measured in the axial direction that is covered in one revolution. In general, a pitch that is too short leads to a very high turn ratio and thus to increased effort during use, since a larger number of rotations must be made to discharge the bone cement. This may result in too much time being required, which is undesirable, particularly during surgery and/or when the bone cement is progressively hardening. In general, a pitch that is too long leads to a low turn ratio and therefore to a very high force for discharging the bone cement. In addition, if the pitch is too steep, the self-locking function may be reduced or eliminated, which in turn unnecessarily complicates operation. The concrete numerical values of these effects depend on different conditions such as the materials used and properties of the respective surfaces.

The extruding apparatus can be made of plastic, or plastic with metal. A complicated mechanism, as in the case of a cartridge press, is not necessary. No levers, bolts, pins, clamps, locking elements, toothed bars and/or gears are required. The forces required to press out the bone cement are lower than those required with conventional extruding apparatuses.

The extruding apparatus according to the invention is easy to handle, since complicated operation of a cartridge press is unnecessary. Discharge is effected simply by rotating the handle.

A thread turn means a helical line of the thread over a distance corresponding to a complete relative rotation of 360°. That is to say, one revolution is considered. The outer surface is the area of the external thread that can contact the corresponding internal thread. The outer surface of a thread turn is composed, for example, of the surface of a first (for example ascending) thread flank, of a second (for example descending) thread flank, of a surface in the region of the peak of the thread, which may, for example, extend in parallel with the longitudinal axis and/or may be located between the thread flanks, and of a further surface in the region of the depression or valley of the thread, which may be located between two thread flanks. These four surfaces are added together over one revolution. In other words, the surface area between two adjacent peaks or valleys of the thread is considered. Roundings or transitions between the individual surfaces are also part of the outer surface. The respective characteristic values for the external thread of the threaded rod can apply accordingly to the internal thread of the adapter unit.

In the case of a trapezoidal thread, for example, the outer surface corresponds to the surfaces of the two thread flanks, the outward-facing surface between them in the region of the thread peak which defines the outer diameter of the external thread, and the outward-facing surface in the region of the thread valley, which defines the inner diameter of the external thread.

In the case of a multi-start thread, the surface areas of all the thread turns are added together over one revolution.

In one embodiment, the extruding apparatus is designed to extrude the bone cement from the first container with an extruding force of at least 0.8 kN, in particular at least 1.0 kN. The extruding force is the force that acts on the bone cement in the first container. In the case of a cartridge press made of metal, for example, an extruding force is 2.5 kN. In the case of small amounts of bone cement for spinal cord applications, however, a significantly lower force is exerted. Preferably, the extruding apparatus is designed such that a cement quantity of between 50 g and 125 g can be extruded within one minute.

In one embodiment, the kit comprises a packaging means. The components of the kit are enclosed in the packaging means, in particular so as to be airtight and/or sterile. The components are the first container, the second container, the mixing apparatus, the extruding apparatus and, if applicable, other components as described. The packaging means is made primarily of plastic. The packaging means can be designed as a blister. A blister comprises, for example, a deep-drawn shell which forms an interior for the arrangement of the components, as well as a cover which is designed in particular as a film. Typically, the cover is planar and therefore extends in a plane. The shell and/or cover of the blister may, but does not necessarily have to, be transparent.

In one embodiment, the first container contains as a first component an amount of at least 40 g of a powder, for example a PMMA bone cement powder. In one embodiment, the second container contains as a second component an amount of at least 18 ml of a liquid, for example a monomer liquid.

In one embodiment, the first container contains an amount of at least 20 g, preferably at least 30 g and/or at most 200 g, preferably at most 120 g, in particular at most 86 g, of the first component. In one embodiment, the second container contains an amount of at least 10 ml, preferably at least 15 ml and/or at most 100 ml, preferably at most 75 ml, in particular at most 50 ml or at most 42 ml of the second component. These amounts have proven to be optimal for the fixation of joint endoprostheses in the bone.

In one embodiment, the second container is arranged in an apparatus for storing and opening the second container. The apparatus for storing and opening the second container is or can be fluidly connected to the first container in order to transfer the second component into the first container.

The apparatus for storing and opening is, on the one hand, designed to store the at least one second container. In particular, the apparatus completely encloses the at least one second container and thus provides mechanical protection. In addition, the apparatus comprises a means for opening the container. In the case of a pouch, this could be a needle or an awl, for example. In the case of an ampoule, this may be a breaking mechanism that separates one part of the ampoule, for example a head of the ampoule, from another part of the ampoule and/or that breaks the ampoule open, for example by buckling or shearing. There may be two pouches, for example on either side of the first container, and optionally two needles. There is typically a seal around a needle, which lies against the wall of the pouch.

The apparatus for storing and opening the second container may comprise a pump, in particular for manual actuation, to pump the liquid into the first container. For example, the apparatus is designed according to EP 3 093 067 B1. This document is incorporated into this application by reference. Alternatively, or additionally, the apparatus for storing and opening the second container can be designed to convey the liquid into the first container by gravity. In this way, use of the kit is possible independently of an external vacuum source. Alternatively, the apparatus can be designed to convey the liquid into the first container by means of a vacuum. For example, the apparatus is designed according to EP 2 404 864 B1 or EP 4 282 518 A1. These documents are incorporated into this application by reference.

This embodiment allows the second container to be opened to transfer the second component into the first container. The connection between the apparatus and the first container is preferably reversible, namely manually detachable. Thus, the apparatus for storage and opening can be detached from the first container after the second component has been transferred, in order to enable or simplify the discharge of the bone cement. Preferably, the apparatus for storing and opening comprises a connecting region, and the first container comprises a connecting region, wherein the two connecting regions can be connected to one another manually and in particular reversibly. In the connected state, the second component can be transferred from the second container into the first container. The connecting region of the first container for connecting the apparatus for storage and opening can be the connecting region of the first container to which the mixing device can also be connected, or another connecting region. In the second case, the two connecting regions of the first container can be arranged on the same side or on opposite sides.

In one embodiment, the first container is arranged separately from the extruding apparatus. In one embodiment, the second container is arranged separately from the extruding apparatus. In particular, the apparatus for storing and opening the second container is arranged separately from the extruding apparatus, together with the second container.

In other words, the given container is arranged spatially separated from the extruding apparatus. The given components can be located in the same space of a packaging means, but are not directly mechanically connected to one another. This allows for a particularly small packing size of the components and thus a small size of the kit. The absolute length of the kit is limited so that space can be saved. The long components of the kit can be arranged in parallel. In particular, a compact shape is achieved in which the length and width of the kit are in similar ranges. For example, the length, as described, is only larger than the width to a limited extent, so that the described advantages arise. In the mechanically connected state of the first container with the extruding apparatus, however, a large length combined with a small width would result, so that these advantages are not achieved.

In one embodiment, the mixing apparatus is at least partially arranged in the first container. The first container with the mixing apparatus and the extruding apparatus are arranged in parallel, preferably one above the other. Typically, the extruding apparatus is arranged at the bottom. In this way, a particularly space-saving arrangement can be achieved. At the same time, an order of use of the components during use of the kit is taken into account. This is the case because the first container with the mixing apparatus and the extruding apparatus are always required one after the other. After the preparation of the bone cement, the user can remove the extruding apparatus, connect it to the first container and extrude the bone cement. This prevents incorrect operation, no additional space is required for temporary storage of components, and components falling is avoided. The described arrangement is located in particular in a packaging means.

In one embodiment, the first container, the second container, the mixing apparatus and the extruding apparatus consist in total of a maximum of 20% steel or a maximum of 20% metal. This reduces the costs, manufacturing effort and weight of the kit. In one embodiment, the said components consist of a maximum of 20% steel or metal or contain no steel and/or no metal. In one embodiment, the extruding apparatus consists of a maximum of 50%, preferably 30%, metal. If no or only a small amount of metal is contained, the kit or its given components can be easily recycled or thermally recycled.

In one embodiment, the adapter unit is or can be mechanically connected to the first container. In one embodiment, the adapter unit has a support surface for standing the adapter unit with the first container on a smooth surface and/or on a holder of the packaging means. The adapter unit can thus serve as a support for the first container. The support surface of the adapter unit can stand on the surface or the holder. The adapter unit has, in particular on the side opposite the support surface, viewed in the axial direction, a connecting region for connecting to the first container. The adapter unit can thus stand on its support surface and hold the first container at the same time. In particular, the packaging means comprises a holder on which the support surface can be placed. In particular, the contours of the holder and the support surface correspond, preferably three-dimensionally, so that a particularly firm hold can be achieved.

In one embodiment, the apparatus for storing and opening the second container comprises a buckling region at which regions of the apparatus can be moved, in particular rotated, relative to one another. The buckling region is designed in such a way that a relative movement leads to a buckling, so that the second container, which is designed in particular as an ampoule, is broken. In particular, the apparatus is designed to be flexible, at least in the buckling region.

In one embodiment, the apparatus for storing and opening the second container comprises an outer shell, an inner shell and a breaking-open element. In general, a breaking-open element is used to break open an ampoule. In particular, each of the two shells surrounds a part of the second container designed as an ampoule. The outer shell and the inner shell are movable relative to each other, in particular displaceable. Given a relative movement of the outer shell and the inner shell, the ampoule moves in relation to the breaking-open element. The breaking-open element can, for example, be designed as described in patent application EP23177510.7 which is incorporated into this application by reference. The breaking-open element can be a shearing element. The shearing element is arranged in such a way that in the event of a relative displacement of the outer shell and the inner shell, it contacts the ampoule, in particular the head of the ampoule, so that the ampoule is opened. The shearing element can typically exert a shearing force on the head of the ampoule, causing the ampoule to break at the intended breaking point. These embodiments allow production of the bone cement in a closed system in which any contact between the user and the components is excluded.

In one embodiment, the kit comprises two first containers that each contain a first component for producing bone cement, two second containers that each contain a second component for producing bone cement, and only one extruding apparatus. The extruding apparatus can optionally be mechanically connected to each of the first two containers, so that prepared bone cement can be extruded from each of the first two containers one after the other using the extruding apparatus. The kit may comprise a mixing apparatus which can be optionally mechanically connected to each of the first two containers in order to mix the two components. Alternatively, the kit may have two mixing apparatuses to allow mixing in each of the two first containers with a separate mixing apparatus.

In one embodiment, the first container, the second container, the mixing apparatus and/or the extruding apparatus are designed as described in EP 2 281 532 B1, EP 2 269 718 B1, EP 3 093 067 B1 and/or EP 22 174 728 A1. Each of these documents is incorporated by reference into this application.

In one embodiment, the first container, the second container, the mixing apparatus and/or the extruding apparatus are designed such that, after opening the second container, monomer liquid can be sucked into the powder by means of an external vacuum, and then both components can be mixed by means of the mixing apparatus which can be operated from the outside. Alternatively or additionally, the transfer of the second component can take place in two steps, wherein the liquid can first flow into a collection volume by the effect of gravity, and is then pumped from there, for example by a manually operated pump plunger, into the first container.

A further aspect of the invention is the use of a kit according to the invention for pressing out bone cement from the first container. In particular, a quantity of at least 50 g and/or a maximum of 130 g of bone cement is pressed out. In particular, the pressing out is done by means of the extruding apparatus. In particular, PMMA bone cement is extruded. In particular, this is done to anchor a joint endoprosthesis in human bone tissue. In particular, the handle of an extruding apparatus is manually rotated so that bone cement is pressed out from the first container. All features, advantages and embodiments of the aforementioned kit and its components and properties also apply to the use and to the method below, and vice versa.

A further aspect of the present invention is a method for using a kit according to the invention. This includes:

mixing the first component and the second component in the first container using the mixing apparatus for the purpose of producing bone cement, removing the extruding apparatus from a packaging means of the kit, and extruding the produced bone cement from the first container using the extruding apparatus.

The method may further comprise one or more of the following steps, in any combination:

opening the packaging means, removing the first container and/or the second container from the packaging means, opening the second container and transferring the second component into the first container, connecting the mixing apparatus to the first container, after the mixing: removing the mixing apparatus from the first container, connecting the extruding apparatus to the first container, connecting a tubular body to the first container for extruding, in particular on a side of the first container opposite the extruding apparatus.

Exemplary embodiments of the invention are also explained in greater detail below with reference to figures. Features of the exemplary embodiments can be combined individually or in a plurality of the claimed subjects, unless otherwise indicated. The claimed scope of protection is not limited to the exemplary embodiments.

DETAILED DESCRIPTION OF THE INVENTION

Figure 2:
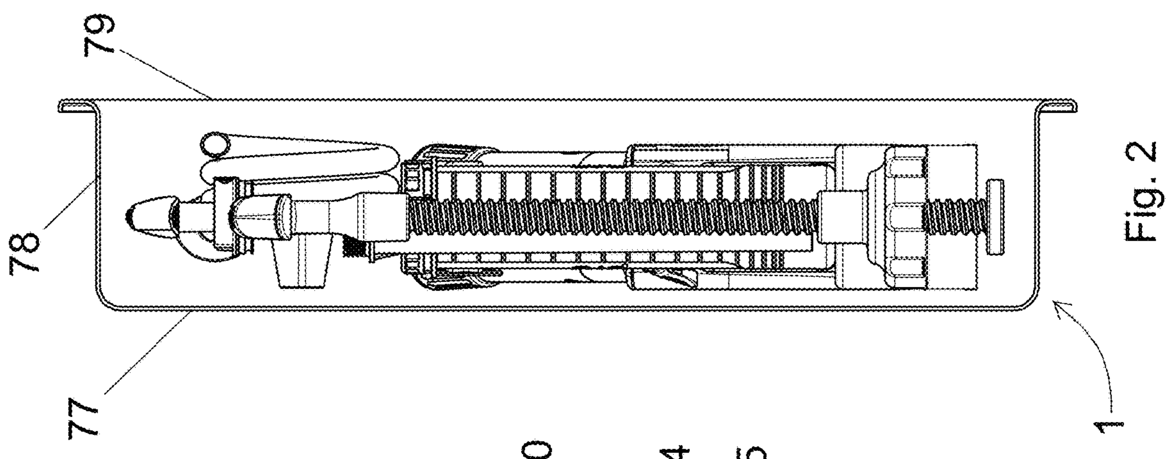
FIG. 2: is a kit according to the invention in side view.
Figure 1:
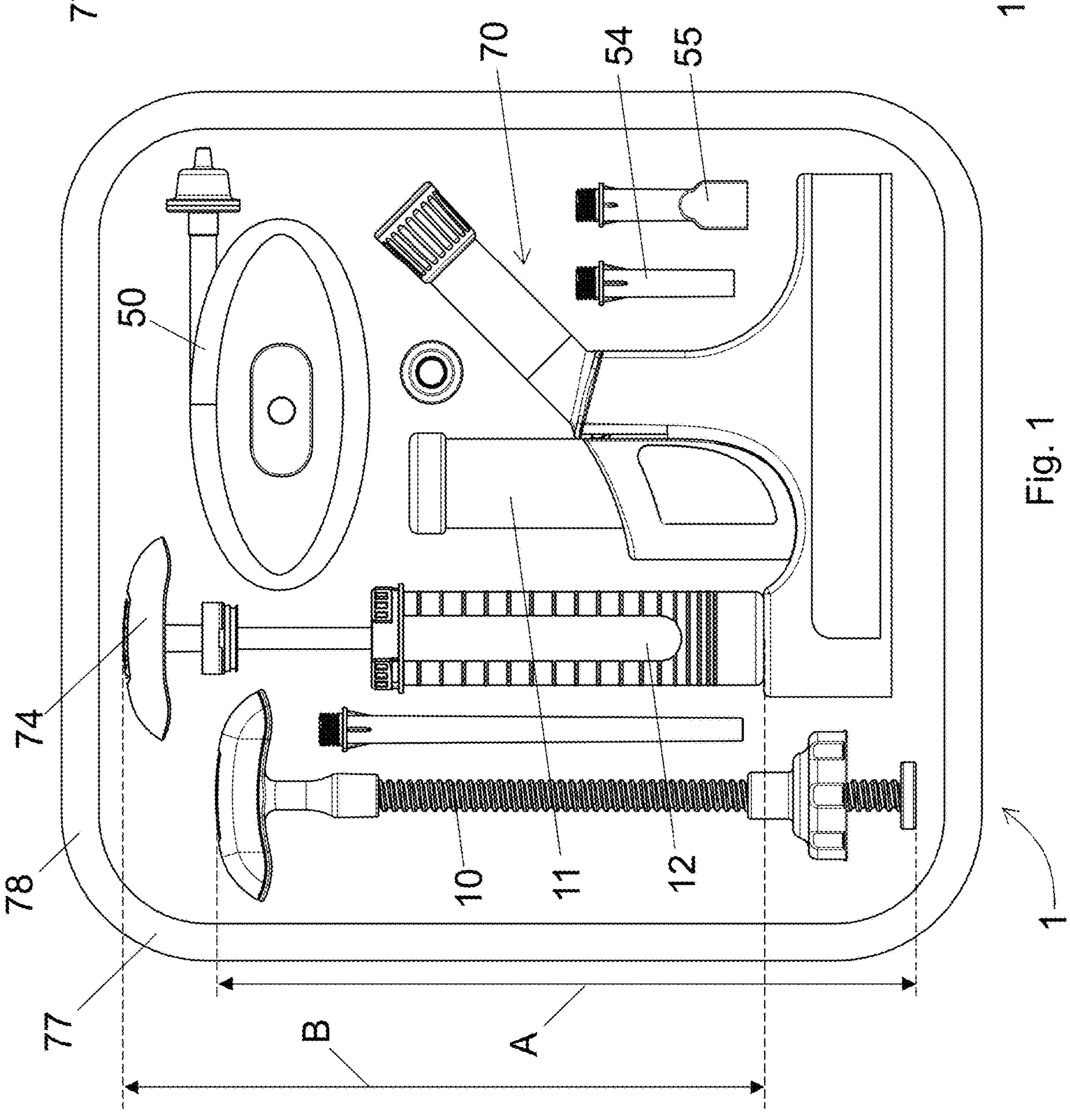
FIG. 1: is a kit according to the invention in plan view.

FIGS. 1 and 2 show a kit 10 according to the invention for producing and extruding bone cement. The kit comprises a first container 12, a second container 70, an extruding apparatus 10 and a mixing apparatus 74. The mixing apparatus 74 is mechanically connected to the first container 12 so that after transferring the second component from the second container 70 into the first container 12 that contains the first component, the two components can be mixed with the mixing apparatus 74 to obtain bone cement. The kit also includes a knee snorkel 54 and a flat snorkel 55 as well as a vacuum hose 50 for connecting the first container 12 to a vacuum source.

The second component can advantageously be sucked into the first container 12 by means of a vacuum. However, with the design shown here, operation without vacuum is also possible. To the right next to the first container 12, a pumping device 11 is arranged which can be used to pump the liquid into the first container. The pumping device can be designed as described in DE 10 2015 106 899 B3, which is incorporated into this application by reference.

The kit further comprises a packaging means 77 in which the components are in particular packed. The packaging means 77 comprises an in particular deep-drawn tray 78 with a widened, circumferential edge and a cover 79 which is attached to the edge, for example welded or glued. The packaging means 77 has a substantially square basic shape.

The mixing apparatus 74 is partially arranged in the first container 12. For the axial extension A of the extruding apparatus 10 and the axial extension B of the first container 12 with the mixing apparatus 74, A/B is between 1.0 and 1.2. In the case shown here, A/B is approximately 1.1.

Figure 3:
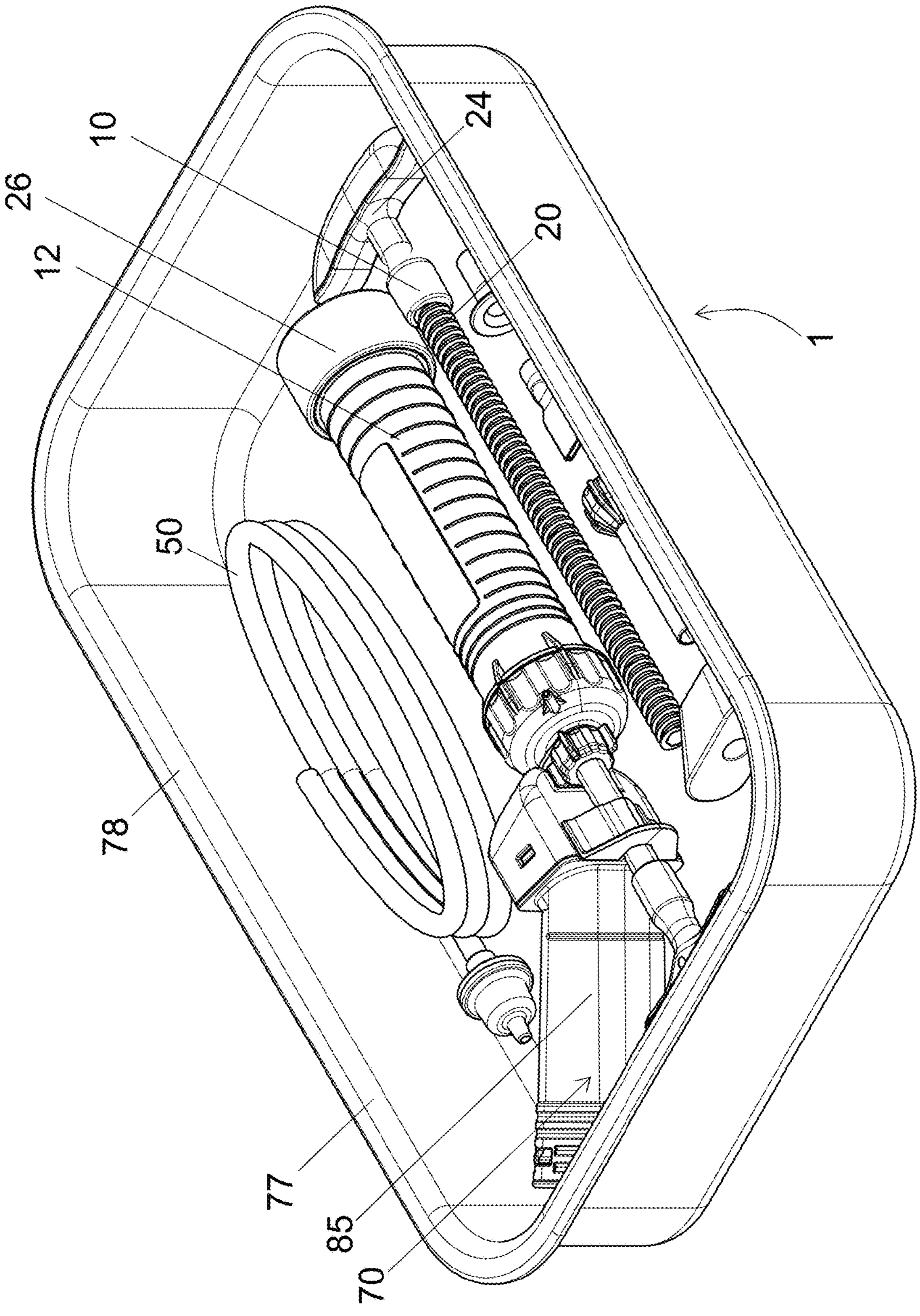
FIG. 3: is a kit according to the invention in a perspective view.
Figure 4:
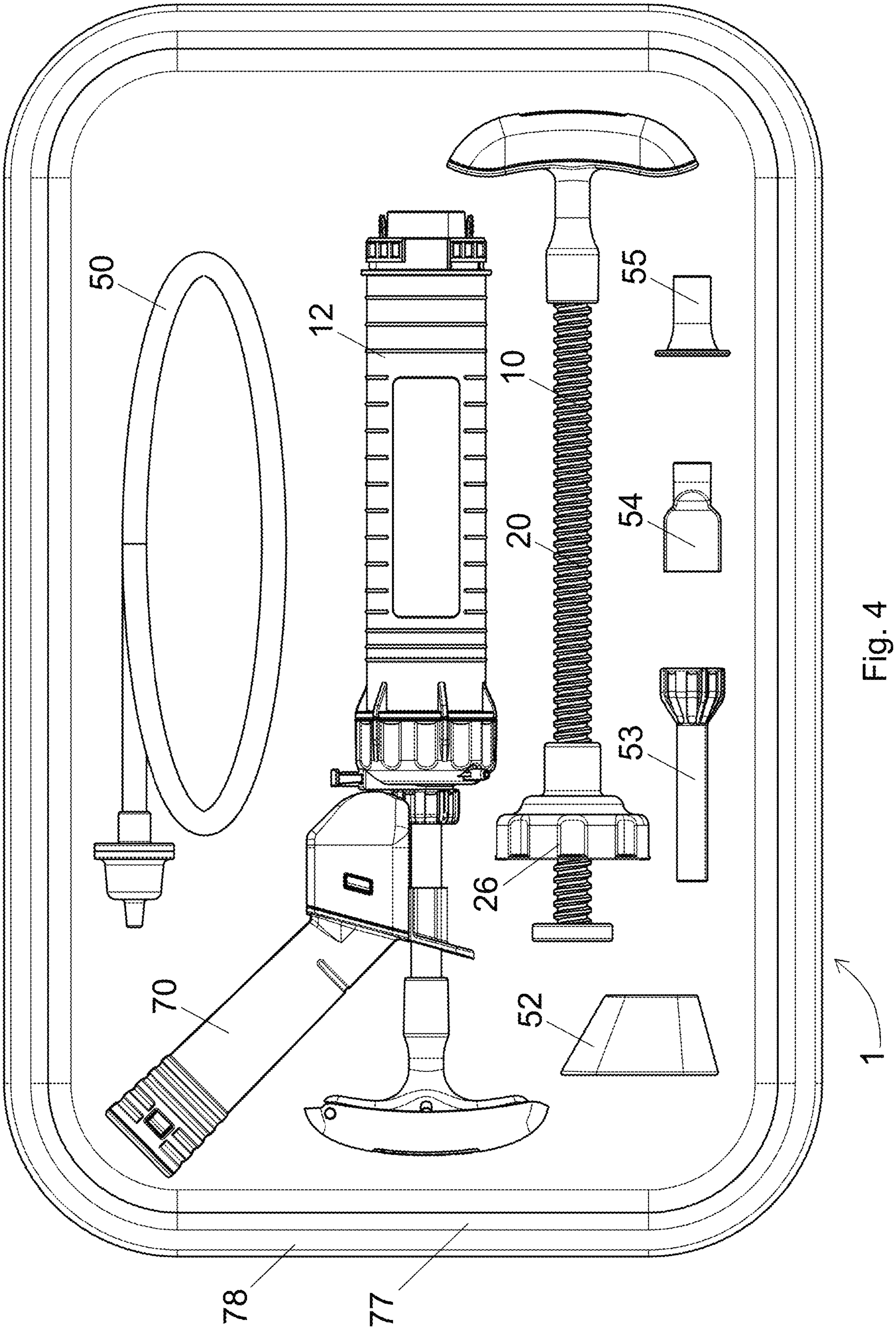
FIG. 4: is a kit according to the invention in plan view.

FIGS. 3 and 4 show other embodiments of a kit 1 in which the packaging means 77 has an elongated basic shape. In the embodiment shown here, the kit 1 includes an apparatus 85 for storing and opening the second container, which contains the second container 70. The apparatus 85 is mechanically connected, in particular reversibly, to the first container 12. This facilitates use because the connection does not have to be established first. FIG. 3 shows a two-part extruding apparatus 10. An adapter unit 26 of the extruding apparatus is mechanically connected to one end of the first container 12, on the side opposite the apparatus 85. A hand part of the extruding apparatus 10 with a threaded rod 20 and handle 24 is arranged separately therefrom and/or next to it. The adapter unit 26 can have, on the side facing away from the first container 12 in relation to the axial extension, a support surface for standing on a smooth surface and/or on a holder of the packaging means (cf. FIGS. 15A to 15C). This makes it easier to stand the first container 12 for mixing and/or after mixing.

In the embodiment shown in FIG. 4, however, the extruding apparatus 10 is arranged completely separately from and/or next to the first container 12. The threaded rod 20 is screwed into the adapter unit 26. The kit 1 further comprises a vacuum hose 50, a knee pressurizer 52, a hip pressurizer 53, a knee snorkel 54 and a flat snorkel 55.

Figure 5:
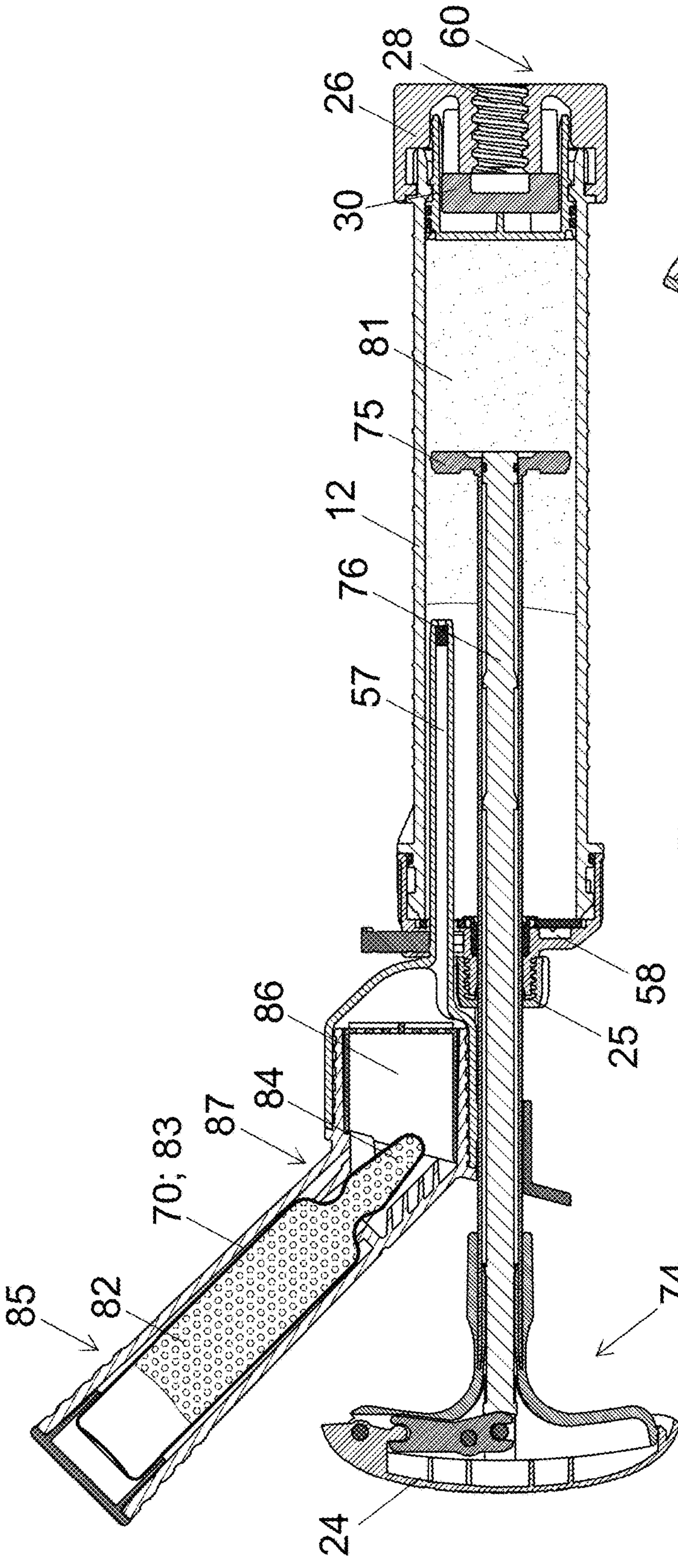
FIG. 5: shows components of a kit according to the invention.

FIG. 5 shows an embodiment of the first container 12, an apparatus 85 for storing and opening the second container 70, and an extruding apparatus 10, for example according to FIG. 3 as described above. The apparatus 85 contains the second container 70 which is designed as an ampoule 83 with a second component 82, namely a monomer liquid. The first component 81 is a bone cement powder which is located in the first container. The apparatus 85 comprises a buckling region 87 at which the apparatus 85 can be buckled in order to break off the head 84 of the ampoule 83. The head 84 and any glass fragments are then retained by a sieve, and the liquid can flow into the second container via the collection volume 86, if applicable a filter element, the tube element 57, and if applicable a further filter element. This can be done by gravity and/or by a vacuum. To apply a vacuum, the first container 12 comprises a nozzle (not shown here; see FIG. 15A) which opens into a vacuum chamber 58. This is connected to the interior of the first container 12 by means of a mesh or sieve. If a vacuum is applied, the liquid is sucked into the interior through the tube element 57.

Figure 6:
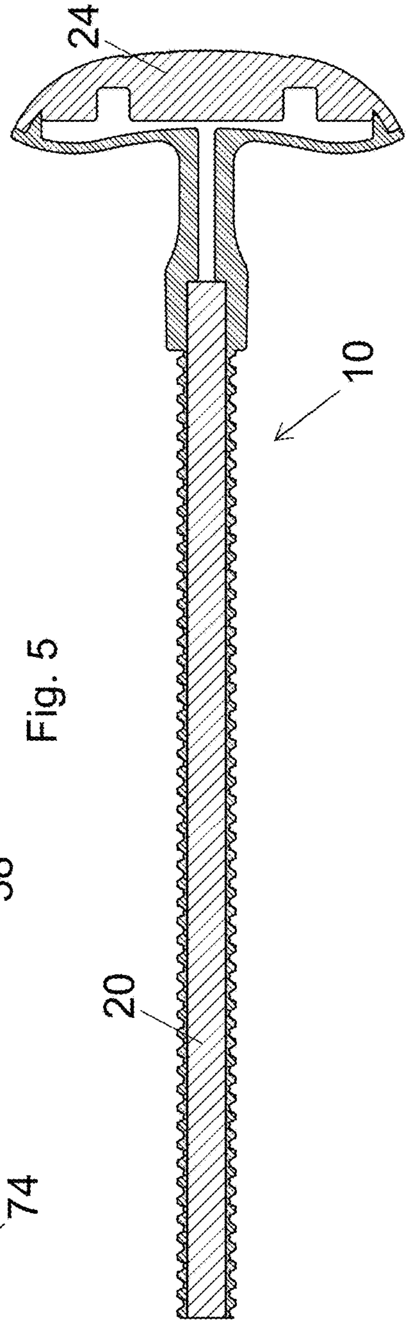
FIG. 6: shows a component of a kit according to the invention.

In the embodiment shown here, the adapter unit 26 of the extruding apparatus comprises a support surface 60. The adapter unit can thus be used to hold the first container 12. For example, the opening of the ampoule 83 and the transfer of the liquid into the first container 12, for example at least partially due to gravity, can take place when the first container 12 is in the standing state by means of the support surface 60. The adapter unit 26 comprises an internal thread 28 for screwing in the threaded rod 20 of the extruding apparatus 10 shown in FIG. 6.

On the opposite side of the first container 12, an adapter unit 25 of the mixing apparatus 74 is arranged. The mixing apparatus 74 further comprises a rod 76 which passes through the adapter unit 25 and connects a mixing element 75 to a handle 24.

Figure 12:
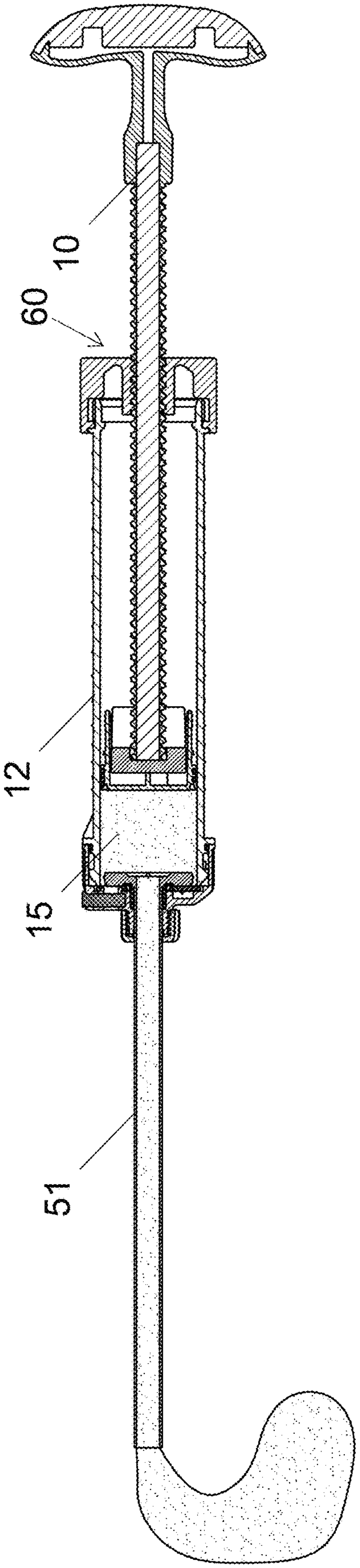
FIG. 12: shows components of a kit according to the invention.

FIG. 5 shows a release mechanism of the mixing apparatus 74. If an actuating element on the handle 24 is actuated in a suitable manner, in particular in the fully pulled-out state, the handle 24 can be released from the rod 76. The rod 76 is designed in this case as a hollow rod. After the handle is released, the rod 76 can be used as a discharge tube for discharging the bone cement. The mixing element 75 remains inside the first container 12, for example in the region of the end face shown on the left, and in particular in a fixed state. This state is also shown in FIG. 12.

Figure 7:
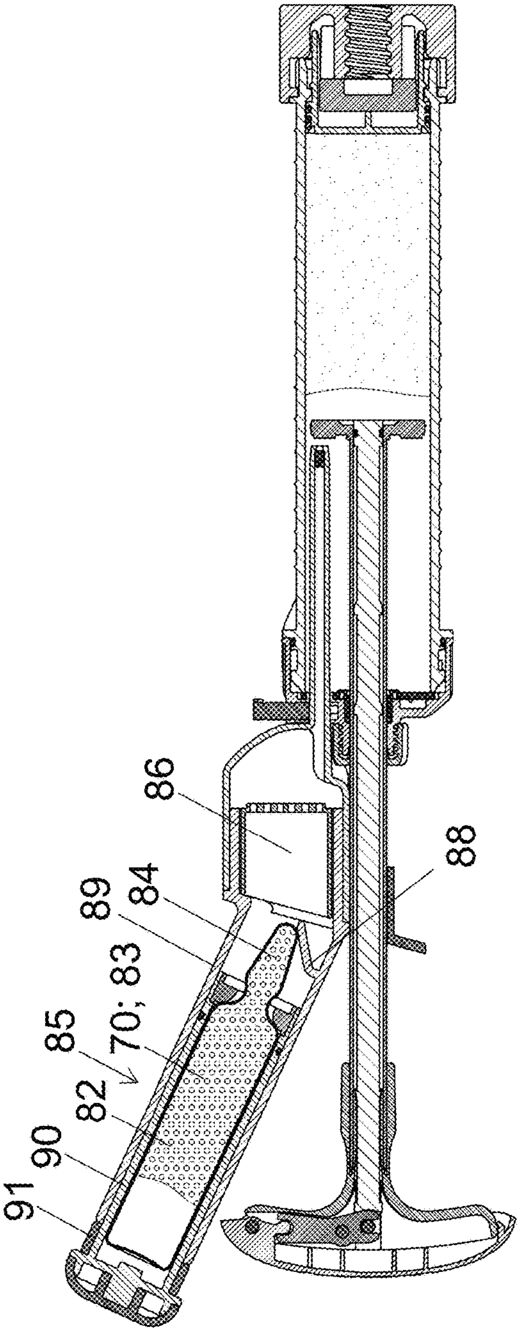
FIG. 7: shows components of a kit according to the invention.
Figure 8:
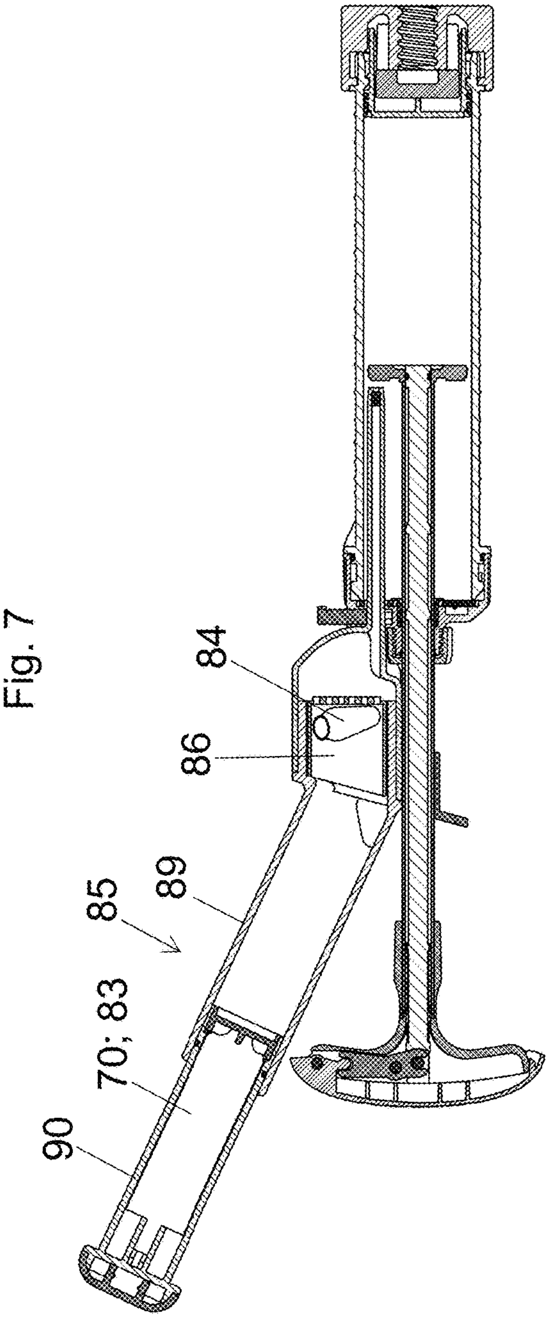
FIG. 8: shows components of a kit according to the invention.

An alternative embodiment of the apparatus 85 for storing and opening the second container 70 is shown in FIGS. 7 and 8. The apparatus 85 comprises an inner shell 90 in which the ampoule 83 is arranged and an outer shell 89 which at least partially surrounds the inner shell 90. The inner shell 90 is axially displaceable with respect to the outer shell 89, at least in the direction of the first container, for example in the manner of a telescope, but can be held by a securing device 91, for example in the form of a removable securing clip. If the securing device 91 is inserted, the movement of the inner shell 90 is blocked. If the securing device is removed, the inner shell 90 can be moved towards the first container. The apparatus 85 further comprises a shearing element 88 for shearing off the head 84 of the ampoule 73. The shearing element typically includes a surface oriented obliquely to the longitudinal extension of the ampoule 83. If the inner shell 90 with the ampoule 83 is pushed towards the first container 12, the head 84 contacts the shearing element 88 and is thereby sheared off.

FIG. 8 shows how, in the embodiment described above or in a similar embodiment, the apparatus 85 comprises an outer shell 89 and an inner shell 90 movable relative to the outer shell 89 and can be used to pump the liquid into the first container 12. By pulling out the inner shell 90, as shown in FIG. 8, the volume in the apparatus 85 is increased, and air flows into the apparatus 85, for example through a suitable valve in a cover of the apparatus 85. When subsequently pushed in, the air displaces the liquid in the apparatus 85, for example in the collection volume 86, which has previously flowed out of the ampoule 83, and presses it into the first container. In this way, a vacuum source can be dispensed with, and the kit can be used for cementing without any additional apparatus.

Figure 9:
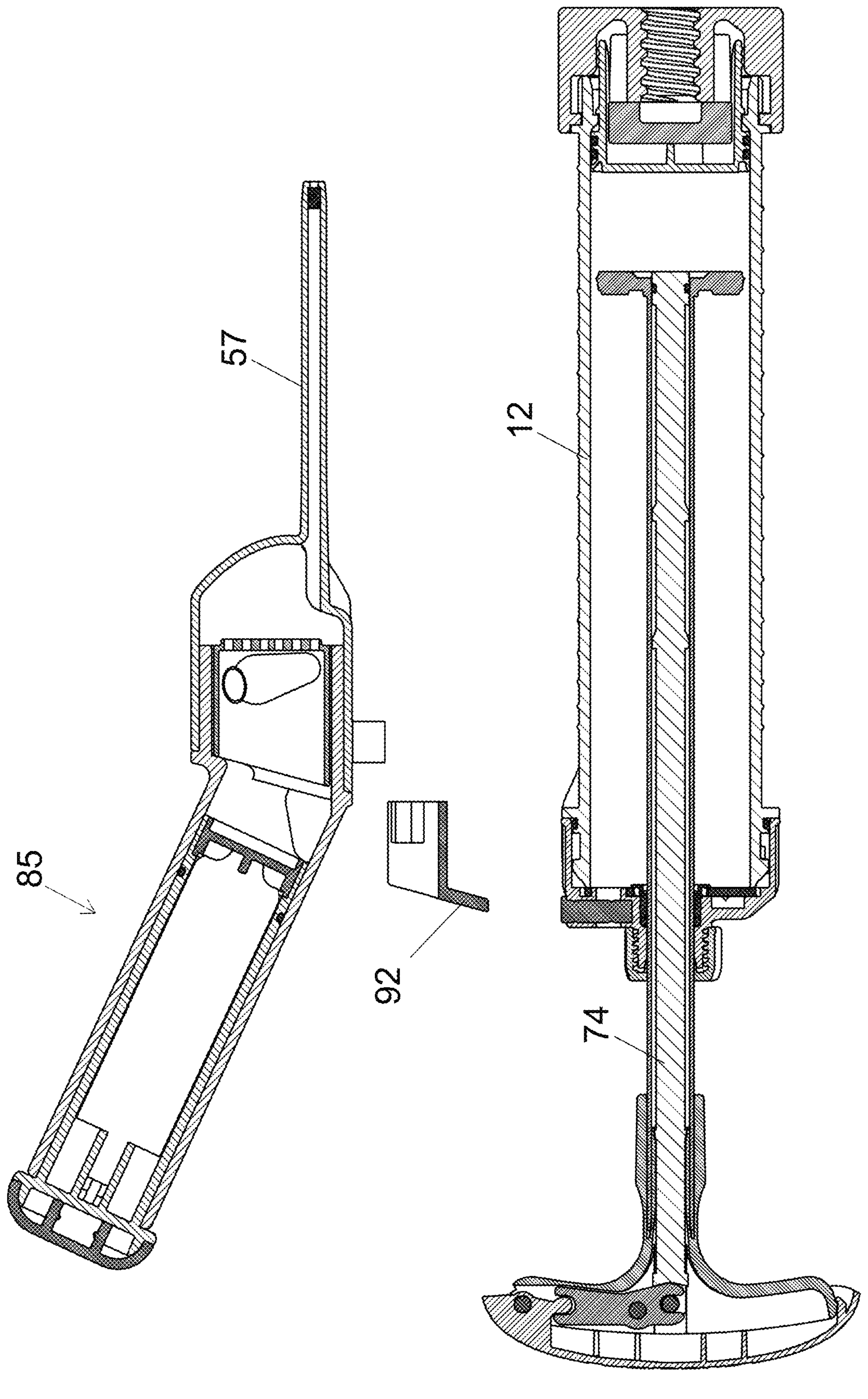
FIG. 9: shows components of a kit according to the invention.

FIG. 9 shows the separation of the apparatus 85 from the first container 12. At least one holding part 92, which has previously established a connection, can be removed. It is then possible to more easily mix and/or extrude the bone cement. The separation can be irreversible. A closure element, for example a gate valve, can close the opening in the first container 12 through which the tube element 57 previously protruded.

Figure 10:
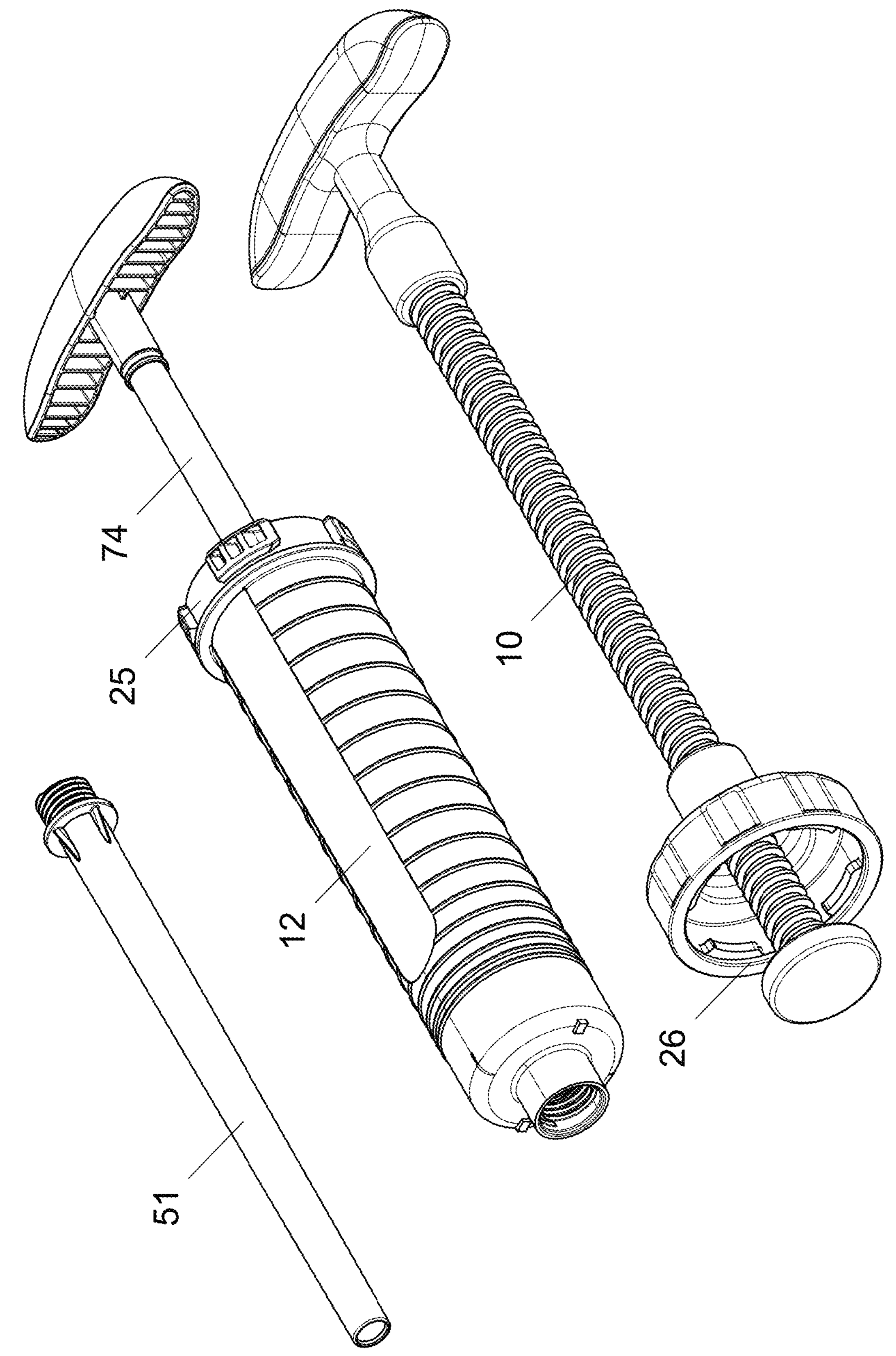
FIG. 10: shows components of a kit according to the invention.

FIG. 10 shows an embodiment in which the mixing apparatus 74 is connected to the first container, and the extruding apparatus 10 and in particular a discharge tube 51 are provided separately therefrom. The mixing apparatus 74 comprises an adapter unit 25, and the extruding apparatus 10 comprises an adapter unit 26. Both adapter units can be attached on the same side of the first container 12. The discharge tube 51 can be attached to the other side of the first container 12.

Figure 11:
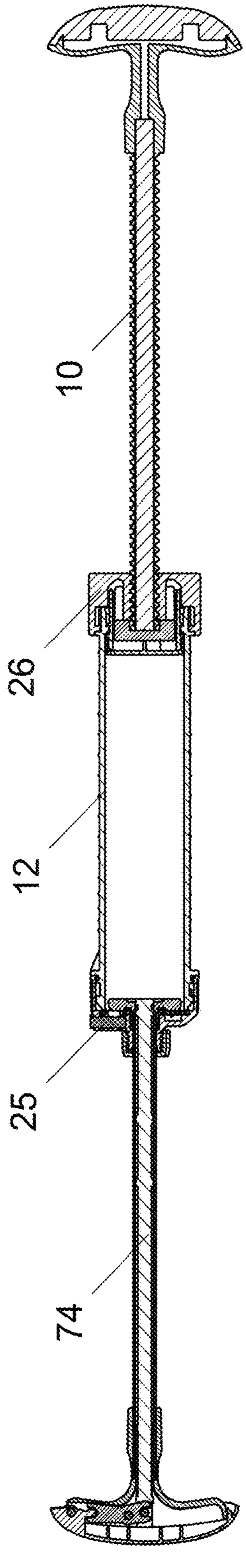
FIG. 11: shows components of a kit according to the invention.

FIG. 11 shows another embodiment in which the adapter unit 25 for the mixing apparatus 74 and the adapter unit 26 for the discharge device are arranged on opposite sides of the apparatus. FIG. 12 shows the extrusion of the bone cement 15 by means of the extruding apparatus 10 through the discharge tube 51.

Figure 13:
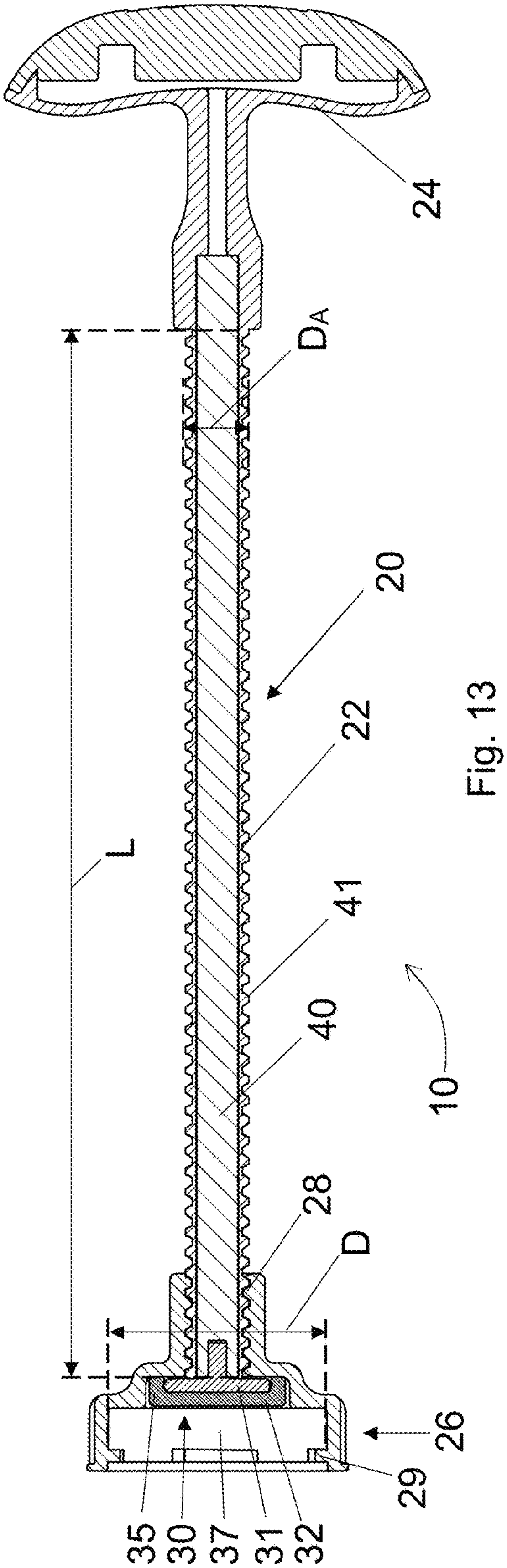
FIG. 13: is a sectional view of an extruding apparatus.
Figure 14:
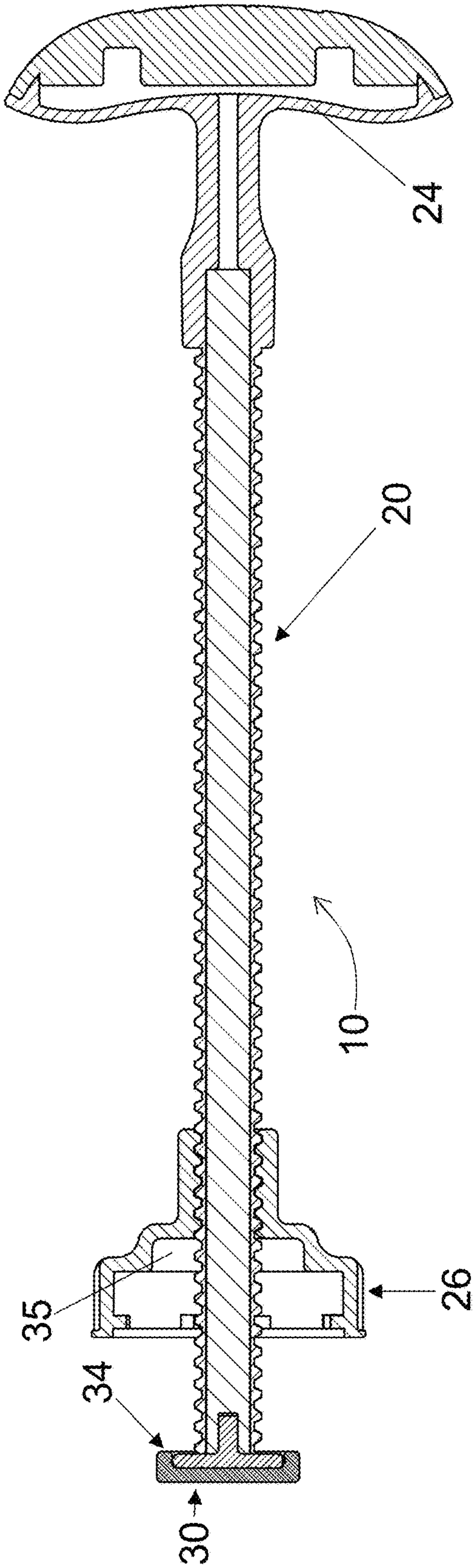
FIG. 14: is a further sectional view of an extruding apparatus.

FIGS. 13 and 14 show a sectional drawing of an extruding apparatus 10 along the central longitudinal axis. The extruding apparatus 10 comprises an adapter unit 26 with a connecting region 37 for mechanically connecting to a first container. In the embodiment shown here, the connecting region 37 can be plugged and/or screwed onto a corresponding region of a first container. In the embodiment shown here, the adapter unit 26 has connecting elements 29 for producing a bayonet connection. The direction of rotation for fastening the bayonet connection corresponds to the direction of rotation for screwing in the threaded rod 20.

The extruding apparatus 10 further comprises a threaded rod 20 with an external thread 22. The threaded rod 20 is passed through the passage opening 27 so that the external thread 22 engages with the internal thread 28 located in the passage opening 27. The manually operated handle 24 for rotating is located on the end of the threaded rod 20 shown at the right. When the threaded rod 20 is rotated, the threaded rod moves axially through the adapter unit 26 so that the bone cement can be pressed out.

On the end of the threaded rod 20 remote from the handle 24, the threaded rod 20 is designed to exert a pressure or a force on the bone cement. For this purpose, a pressure element 30 may be present. The pressure element 30 serves to directly or indirectly exert pressure on bone cement in order to press it out of a first container. For example, the pressure element 30 can move a plunger of the first container, which in turn presses the bone cement out of the first container. The pressure element 30 is discussed in detail below.

The threaded rod 20 can have an inner core, in the example shown here a metal rod 40, and/or a casing, in the example shown here a plastic casing 41. The metal rod 40 runs centrally inside the threaded rod 20 and contributes significantly to the mechanical stability of the threaded rod 20. The plastic casing 41 forms the external thread 22 and protects the metal rod 40 from external influences. The metal rod 40 is preferably not rotationally symmetrical, in order to ensure a connection to the handle 24 and/or the casing for conjoint rotation.

For example, the metal rod 40 can be hexagonal or square. In particular, a metal rod 40 with or made of stainless steel such as 316L is used. In particular, the metal rod 40 is completely encased with a plastic material. In particular, the thread is made of plastic. This provides a particularly smooth thread. The metal rod 40 is protected from external influences. In one embodiment, the metal rod 40 has a diameter of at least 7 mm and/or at most 10 mm, preferably about or exactly 8 mm.

In one embodiment, the threaded rod 20 has a length L of at least 15 cm and/or at most 23 cm. The length of the threaded rod 20 is in particular at least 17 cm, preferably at least 19 cm and/or at most 23 cm, preferably at most 21 cm. The length L is measured between the outermost regions where the external thread 22 is present. In addition, the outer diameter $D_A$ of the threaded rod 20 is shown, which is measured in the radial direction between the peaks of the external thread 22. The outer diameter $D_A$ in the example shown here is between 13.5 mm and 15 mm.

In one embodiment, the adapter unit comprises a connecting region for plugging onto a first container. In one embodiment, the connecting region has an inner diameter of at least 3.3 cm and/or at most 4.0 cm. In one embodiment, the threaded rod contains no metal parts other than the metal rod.

In FIG. 13, a completely unscrewed position of the threaded rod 20 from the adapter unit 26 is shown. In contrast, FIG. 14 shows a position in which the threaded rod 20 has already been partially rotated through the adapter unit 26, as occurs when pressing out bone cement.

In one embodiment, the adapter unit 26 comprises a recess 35 into which the pressure element 30 can be completely received. In this way, the connecting region 37 of the adapter unit 26 shown on the left side remains free of the pressure element 30. The connecting region 37 can thus be slipped over the associated end of the first container or plugged or screwed onto it without disturbing the pressure element 30.

The pressure element 30 can be constructed in two parts, as shown in FIGS. 13 and 14. A first part 31 in this case can be tightly connected to the threaded rod 20 so that it rotates together with the threaded rod 20 when the same rotates. A second part 32 can be rotatably connected to the first part 31 so that the second part 32 does not rotate when the threaded rod 20 is rotated. In this way, no rotational movement, but only an axial pressure force, is exerted on the bone cement 15 and/or on the plunger. The contacting surfaces of the first part 31 and of the second part 32 are preferably flat and smooth to enable smooth rotation.

In the example shown here, the second part 32 of the pressure element 30 surrounds the first part 31 of the pressure element 30 and/or forms an undercut 34 therewith. On the right-hand side, the circumferential outer rim of the second part 32 extends inwards and engages behind the radially outer edge of the first part 31. The first part 31 and/or the second part 32 can be designed in the form of a plate. The second part 32 may have a diameter of at least 20 mm and/or at most 30 mm, for example approximately or exactly 25 mm.

Figure 15C:
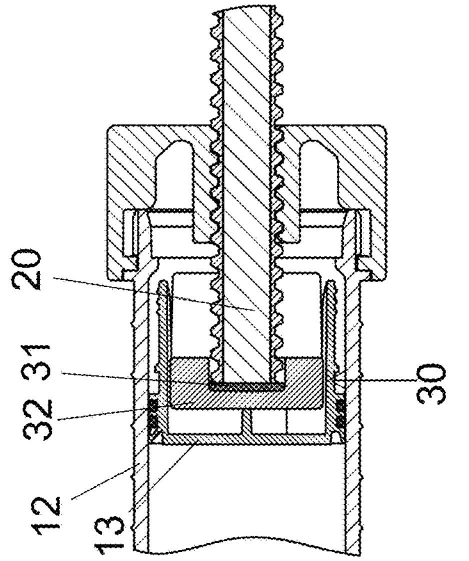
FIGS. 15A-15C: show details of an extruding apparatus in a first container.
Figure 15B:
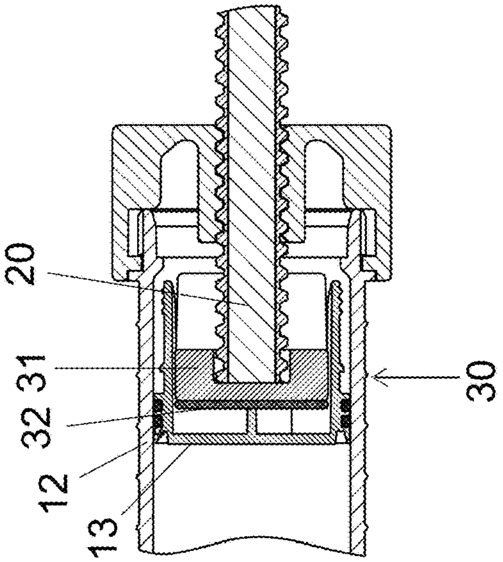
Figure 15A:
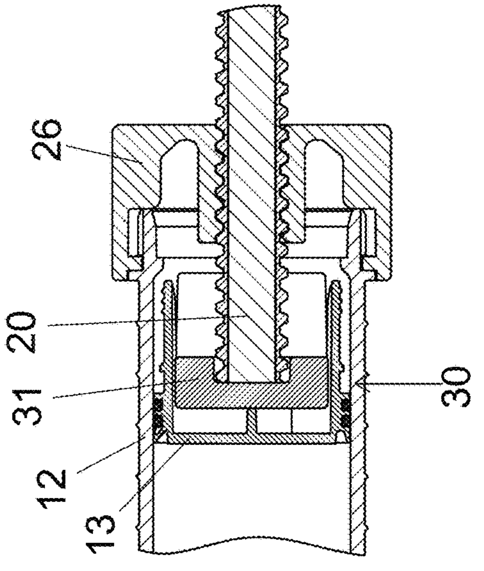

Different embodiments of the pressure element 30 are shown in FIGS. 15A to 15C. In principle, the pressure element 30 presses on the bone cement to press it out. In particular, this is done indirectly, with the pressure element 30 pressing on a plunger 13 which in turn is in contact with the bone cement. In FIG. 15A, the pressure element 30 comprises only a first part 31 which is fixedly or rotatably connected to the threaded rod 20. The structure is particularly simple. However, the plunger 13 may also rotate, which increases the friction and thus the force required for extruding. FIG. 15B shows a two-part construction of the pressure element 30. Between the first part 31 and the plunger 13, there is a second part 32 of the pressure element 32 which is arranged rotatably with respect to the first part 31. The second part 32 extends over almost the entire inner diameter of the corresponding region of the plunger, wherein advantageously at least a slight distance should remain between the inner peripheral surface of the plunger 13 and the second part 32 so that no friction occurs here. The second part 32 may be a flat disk. In particular, there is a lubricant, such as silicone, between the two parts 31, 32 to enable smooth rotation. The first part 31 can be connected to the threaded rod 20 in a rotationally fixed manner. There is a rotation between the first part 31 and the second part 32, but no rotation between the second part 32 and the plunger 13. This reduces friction and therefore the required force. FIG. 15C shows a further embodiment in which the first part 31 is designed as a flat disk which is located in a recess of the second part 32. The threaded rod only rotates the flat first part 31, and the second part 32 does not rotate with the plunger 13. The parts 31, 32 transmit the force of the extruding apparatus evenly and prevent the plunger 13 from tilting.

Figure 16:
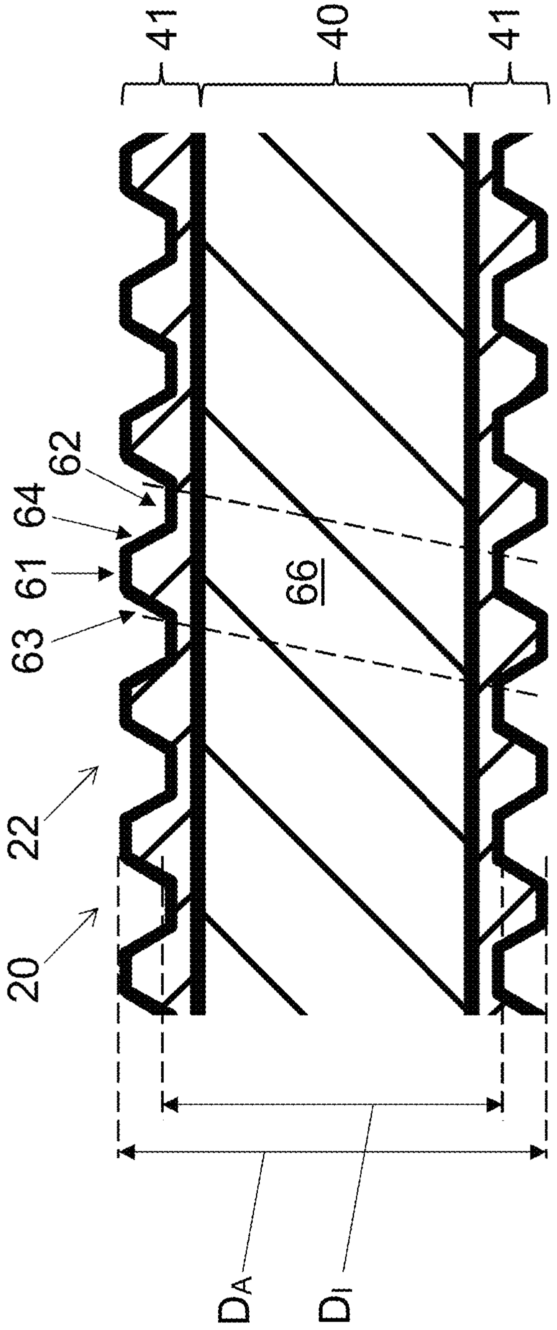
FIG. 16: shows an enlarged detail of a threaded rod.

FIG. 16 is an enlarged section through a threaded rod 20. This comprises an internal metal rod 40 and a plastic casing 41 which completely encloses the metal rod 40. The outer diameter DA of the threaded rod 20 is shown, which corresponds to the maximum diameter between the peaks on both sides of the external thread 22. In addition, the inner diameter DI of the threaded rod 20 is shown, which corresponds to the minimum diameter between the depressions or valleys on both sides of the external thread 22. The thread has a thread depth between 1 mm and 2 mm. The difference between the inner diameter $D_I$ and the outer diameter $D_A$ is therefore between 2 mm and 4 mm.

A thread turn 66 is delimited by dashed lines by way of example. The thread turn corresponds to a complete rotation of the external thread 22 in relation to the corresponding internal thread. The threaded rod 20 can be designed such that an outer surface of a thread turn 66 of the external thread 22 is at most 370 $mm^2$. In the example of a trapezoidal thread shown here, the outer surface of the thread is determined as the sum of the upper surface 61, which corresponds to the surface in the region of the thread peak, the lower surface 62, which corresponds to the surface in the region of the thread depression, the first (ascending) flank surface 63 and the second (descending) flank surface 64.

In one embodiment, an outer surface of a thread turn of the external thread is at most 450 $mm^2$, at most 430 $mm^2$, at most 400 $mm^2$, at most 370 $mm^2$, at most 350 $mm^2$, at most 330 $mm^2$, or at most 300 $mm^2$. In one embodiment, an outer surface of a thread turn of the external thread is at least 100 $mm^2$, at least 130 $mm^2$, at least 160 $mm^2$, at least 180 $mm^2$, at least 200 $mm^2$, at least 215 $mm^2$, at least 250 $mm^2$, at least 280 $mm^2$, at least 320 $mm^2$, or at least 350 $mm^2$. These values may be particularly suitable depending on the design and materials.

In an example, the threaded rod has an outer diameter $D_A$ of 14 mm, a thread depth (tooth height) of 1.5 mm and a pitch of 4.5 mm. These values represent a good compromise between advancement per rotation and the force required to turn. In addition, this threaded rod 20 has a suitable self-locking mechanism, so that it has no tendency to turn back during the extruding.

Figure 17C:
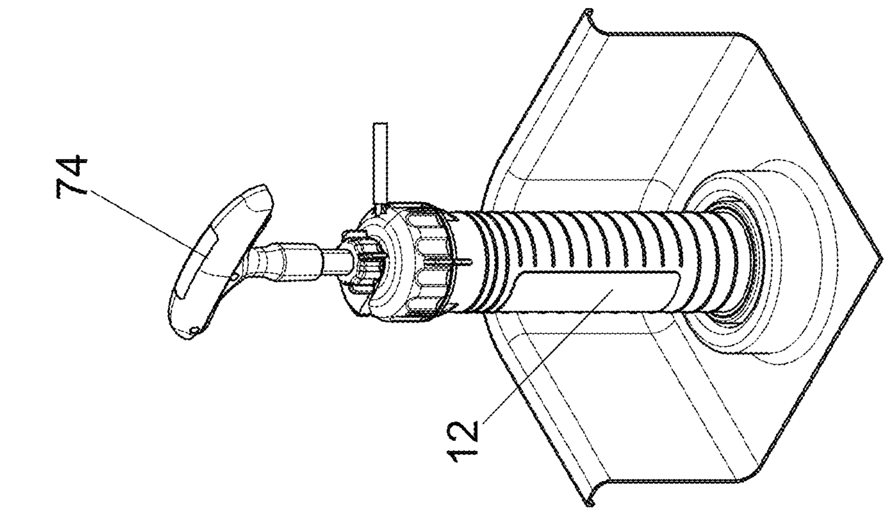
FIGS. 17A-17C: are several views of a first container on or in a packaging means.
Figure 17B:
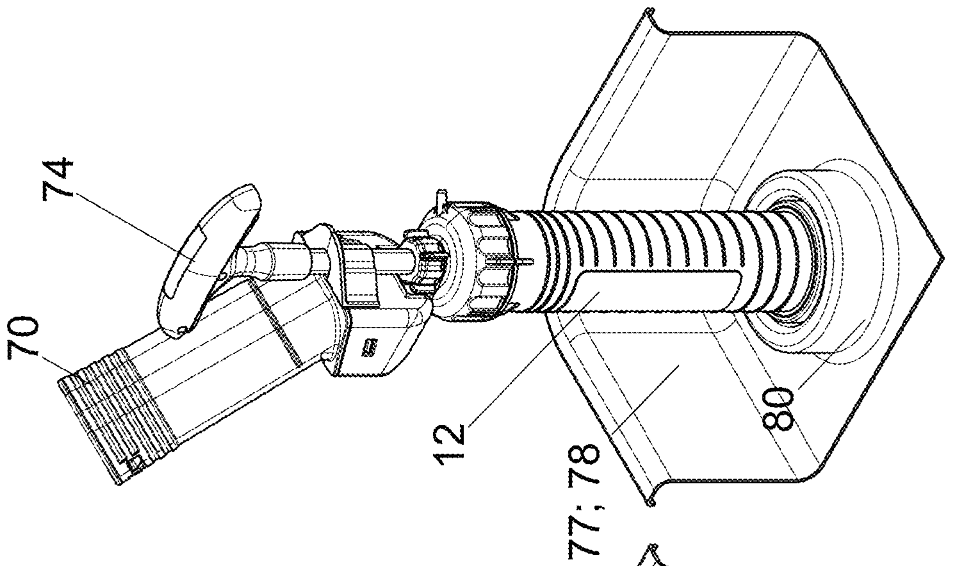
Figure 17A:
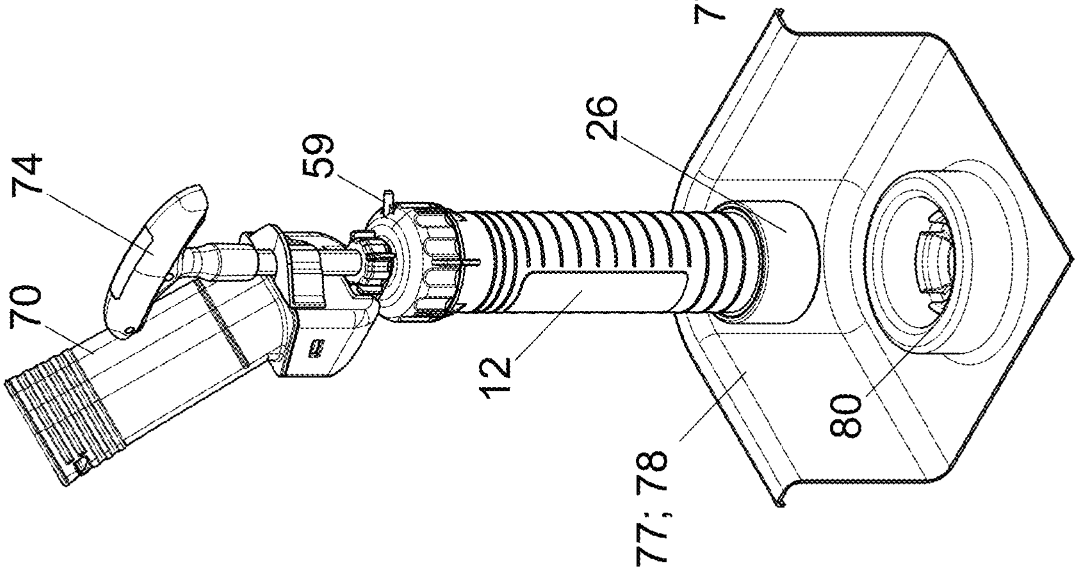

FIGS. 17A to 17B show the use of a holder 80 in the packaging means 77. An adapter unit 26, in particular an extruding apparatus 10, is connected to the first container 12 on its side facing away from the apparatus 85. The adapter unit 26 comprises a support surface 60. The support surface 60 corresponds to the holder 80 which is arranged or formed on the inside of the packaging means 77, for example by deep drawing. Both the support surface 60 and the holder 80 are designed as three-dimensional structures that ensure good interlocking and thus a stable hold. If, however, the adapter unit 26 is contrastingly designed as a hollow cylinder, standing on a flat surface is possible.

FIG. 17A shows the state shortly before standing the first container 12 on the support surface 80. FIG. 17B shows the standing state. The apparatus for storing and opening the second container is connected the second container 70, and the mixing apparatus is connected to the first container. In FIG. 17C, the mentioned apparatuses are removed. Now the mixing can begin. Due to the firm and secure standing of the first container 12, this can be done particularly easily and safely.

List of Reference Numerals

Kit 1
Extruding apparatus 10
Pumping device 11
First container 12
Plunger 13
Bone cement 15
Threaded rod 20
External thread 22
Handle 24
Adapter unit 25
Adapter unit 26
Passage opening 27
Internal thread 28
Connecting element 29
Pressure element 30
First part 31
Second part 32
Undercut 34
Recess 35
Connecting region 37
Metal rod 40
Plastic casing 41
Vacuum hose 50
Discharge tube 51
Knee pressurizer 52
Hip pressurizer 53
Knee snorkel 54
Flat snorkel 55
Tube element 57
Vacuum chamber 58
Nozzle 59
Support surface 60
Upper surface 61
Lower surface 62
First flank surface 63
Second flank surface 64
Thread turn 66
Second container 70
Mixing apparatus 74
Mixing element 75
Rod 76
Packaging means 77
Shell 78
Cover 79
Holder 80
First component 81
Second component 82
Ampoule 83
Head 84
Apparatus 85
Collection volume 86
Buckling region 87
Shearing element 88
Outer shell 89
Inner shell 90
Securing device 91
Holding part 92
Inner diameter D
Inner diameter $D_I$
Outer diameter $D_A$
Length L Axial extension A
Axial extension B1

The invention claimed is:

1. A kit for producing and extruding bone cement, comprising:

a first container which contains a first component for producing bone cement, a second container which contains a second component for producing bone cement, a mixing apparatus for manually mixing the first component and the second component in the first container for the purpose of producing bone cement, an extruding apparatus for manually extruding the produced bone cement from the first container, wherein the extruding apparatus comprises a threaded rod with an external thread, a handle for rotating the threaded rod, and an adapter unit for mechanically connecting to the first container, wherein the adapter unit comprises a passage opening with an internal thread for the threaded rod.

2. The kit according to claim 1 wherein the mixing apparatus is at least partially arranged in the first container, wherein the extruding apparatus has an axial extension A, and the first container with the mixing apparatus has an axial extension B, wherein, for the ratio A/B, the following applies:

$$A/B \geq 0.9 \text{ and/or } A/B \leq 1.5.$$

3. The kit according to claim 1 wherein the extruding apparatus is designed to extrude the bone cement from the first container with an extruding force of at least 0.7 kN.

4. The kit according to claim 1 wherein the kit comprises a packaging means, and the components of the kit are enclosed in the packaging means.

5. The kit according to claim 1 wherein the first container contains as the first component an amount of at least 40 g of a PMMA bone cement powder, and/or in that the second container contains as the second component an amount of at least 18 ml of a monomer liquid.

6. The kit according to claim 1 wherein the second container is arranged in an apparatus for storing and opening the second container, wherein the apparatus for storing and opening the second container is fluidically connected to the first container in order to transfer the second component into the first container.

7. The kit according to claim 6 wherein the apparatus for storing and opening the second container:

comprises a buckling region for buckling the apparatus such that the second container can be opened by buckling, or comprises an outer shell, an inner shell, and a shearing element, wherein the outer shell and the inner shell are displaceable relative to each other, and the second container is moved by the relative displacement with respect to the shearing element in order to open the second container by shearing a part of the second container.

8. The kit according to claim 1 wherein the first container and/or the second container is arranged separately from the extruding apparatus.

9. The kit according to claim 1 wherein the mixing apparatus is at least partially arranged in the first container, wherein the first container with the mixing apparatus and the extruding apparatus are arranged in parallel.

10. The kit according to claim 1 wherein the first container, the second container, the mixing apparatus and the extruding apparatus consist in total of a maximum of 20% metal.

11. Use of a kit according to claim 1 for pressing out an amount of between 50 g and 130 g of bone cement from the first container.

12. A method for using a kit according to claim 1, comprising:

mixing the first component with the second component in the first container using the mixing apparatus for the purpose of producing bone cement, removing the extruding apparatus from a packaging means of the kit, extruding the produced bone cement from the first container using the extruding apparatus.

13. The kit according to claim 1 wherein the extruding apparatus is designed to extrude the bone cement from the first container with an extruding force of at least 1.0 kN.

14. The kit according to claim 1 wherein the kit comprises a packaging means, and the components of the kit are enclosed in the packaging means so as to be airtight or sterile.

15. The kit according to claim 1 wherein the mixing apparatus is at least partially arranged in the first container, wherein the first container with the mixing apparatus and the extruding apparatus are arranged one above the other.

* * * * *